United States Patent
Rao et al.

(10) Patent No.: US 9,072,496 B2
(45) Date of Patent: Jul. 7, 2015

(54) METHOD AND SYSTEM FOR MODELING AND PROCESSING FMRI IMAGE DATA USING A BAG-OF-WORDS APPROACH

(71) Applicants: International Business Machines Corporation, Armonk, NY (US); University of Central Florida Research Foundation, Inc., Orlando, FL (US)

(72) Inventors: Ravishankar Rao, Elmsford, NY (US); Soumyabrata Dey, Orlando, FL (US); Mubarak Shah, Oviedo, FL (US); Solmaz Berkan, Oviedo, FL (US)

(73) Assignees: International Business Machines Corporation, Armonk, NY (US); University of Central Florida Research Foundation, Inc., Orlando, FL (US)

( * ) Notice: Subject to any disclaimer, the term of this patent is extended or adjusted under 35 U.S.C. 154(b) by 214 days.

(21) Appl. No.: 13/757,102

(22) Filed: Feb. 1, 2013

(65) Prior Publication Data
US 2013/0211229 A1 Aug. 15, 2013

Related U.S. Application Data

(60) Provisional application No. 61/593,946, filed on Feb. 2, 2012.

(51) Int. Cl.
*G06K 9/00* (2006.01)
*A61B 5/00* (2006.01)
*G06T 7/00* (2006.01)
(Continued)

(52) U.S. Cl.
CPC ............... *A61B 5/7264* (2013.01); *A61B 5/055* (2013.01); *A61B 5/7225* (2013.01); *A61B 5/7246* (2013.01); *A61B 5/0042* (2013.01); *A61B 5/168* (2013.01); *G06T 7/0012* (2013.01); *G06T 2207/10076* (2013.01); *G06T 2207/10088* (2013.01); *G06T 2207/20081* (2013.01); *G06T 2207/30016* (2013.01); *G06K 9/4676* (2013.01)

(58) Field of Classification Search
CPC .......... G06T 2207/10076; G06T 2207/10084; G06T 2207/10081; G06T 2207/10088; G06T 2207/30048; G06T 2207/30068; G06T 2207/10072; G06T 2207/30004; G06T 2207/30016; G06T 7/0012; G06T 7/0024
USPC ......................................................... 382/128
See application file for complete search history.

(56) References Cited

U.S. PATENT DOCUMENTS

2003/0068074 A1* 4/2003 Hahn .............................. 382/128
2012/0010513 A1* 1/2012 Wong et al. .................... 600/476

OTHER PUBLICATIONS

S.M. Smith, "Overview of fMRI Analysis," The British Journal of Radiology, Dec. 2004, pp. S167-S175, vol. 77, No. 2.
(Continued)

*Primary Examiner* — Ali Bayat
(74) *Attorney, Agent, or Firm* — Vazken Alexanian; Ryan, Mason & Lewis, LLP

(57) ABSTRACT

Systems and methods for processing image data are provided. A computer implemented method for processing image data, comprises gathering 4-D image data from a subject, extracting time series data, and spatial and degree data of each voxel of the subject, deriving at least one feature from the time series data, deriving at least one feature from the spatial and degree data, combining the at least one feature from the time series data, and the at least one feature from the spatial and degree data to generate combined data, and inputting the combined data to a classifier, wherein the classifier outputs a classification based on the combined data.

25 Claims, 7 Drawing Sheets

(51) Int. Cl.
G06K 9/46 (2006.01)
A61B 5/055 (2006.01)
A61B 5/16 (2006.01)

(56) References Cited

OTHER PUBLICATIONS

M.E. Raichle et al., "A Default Mode of Brain Function," Proceedings of the National Academy of Sciences (PNAS) of the United States of America, Jan. 2001, pp. 676-682, vol. 98, No. 2.

Marcus E. Raichle, "The Brain's (Dark Energy)," Scientific American, Mar. 2010, pp. 44-49, vol. 302, No. 3.

D.H. Weissman et al., "The Neural Bases of Momentary Lapses in Attention," Nature Neuroscience, Jul. 2006, pp. 971-978, vol. 9, No. 7.

F.X. Castellanos et al., "Quantitative Brain Magnetic Resonance Imaging in Attention-Deficit Hyperactivity Disorder," Archives of General Psychiatry, Jul. 1996, pp. 607-616, vol. 53, No. 7.

S. Overmeyer et al., "Distributed Grey and White Matter Deficits in Hyperkinetic Disorder: MRI Evidence for Anatomical Abnormality in an Attentional Network," Psychological Medicine,, 2001, pp. 1425-1435, vol. 31, No. 8.

E.R. Sowell et al., "Cortical Abnormalities in Children and Adolescents with Attention-Deficit Hyperactivity Disorder," The Lancet, Nov. 2003, pp. 1699-1707, vol. 362, No. 9397.

L.J. Seidman et al., "Dorsolateral Prefrontal and Anterior Cingulate Cortex Volumetric Abnormalities in Adults with Attention-Deficit/Hyperactivity Disorder Identified by Magnetic Resonance Imaging," Biological Psychiatry, Nov. 2006, pp. 1071-1080, vol. 60, No. 10.

G. Bush et al., "Anterior Cingulate Cortex Dysfunction," Biological Psychiatry, Jun. 1999, pp. 1542-1552, vol. 45, No. 12.

S. Durston et al., "Differential Patterns of Striatal Activation in Young Children With and Without ADHD," Biological Psychiatry, May 2003, pp. 871-878, vol. 53, No. 10.

M.H. Teicher et al., Functional Deficits in Basal Ganglia of Children With Attention-Deficit/Hyperactivity Disorder Shown With Functional Magnetic Resonance Imaging Relaxometry, Apr. 2000, pp. 470-473, vol. 6, No. 4.

F.X. Castellanos et al., "Cingulate-Precuneus Interactions: A New Locus of Dysfunction in Adult Attention-Deficit/Hyperactivity Disorder," Biological Psychiatry, Feb. 2008, pp. 332-337, vol. 63, No. 3.

L. Tian et al., "Altered Resting-State Functional Connectivity Patterns of Anterior Cingulate Cortex in Adolescents With Attention Deficit Hyperactivity Disorder," Neuroscience Letters, May 2006, pp. 39-43, vol. 400, Nos. 1-2.

Q. Cao et al., "Abnormal Neural Activity in Children With Attention Deficit Hyperactivity Disorder: A Resting-State Functional Magnetic Resonance Imaging Study," NeuroReport, Jul. 2006, pp. 1033-1036, vol. 17, No. 10.

Z. Yu-Feng et al., "Altered Baseline Brain Activity in Children With ADHD Revealed by Resting-State Functional MRI," Brain & Development, Mar. 2007, pp. 83-91, vol. 29, No. 2.

C.-Z. Zhu et al., "Fisher Discriminative Analysis of Resting-State Brian Function for Attention-Deficit/Hyperactivity Disorder," NeuroImage, Mar. 2008, pp. 110-120, vol. 40, No. 1.

T. Leung et al., "Representing and Recognizing the Visual Appearance of Materials Using Three-Dimensional Textons," International Journal of Computer Vision, Jun. 2001, pp. 29-44, vol. 43, No. 1.

L. Fei-Fei et al., "A Bayesian Hierarchical Model for Learning Natural Scene Categories," IEEE Computer Society on Computer Vision and Pattern Recognition (CVPR), Jun. 2005, pp. 524-531, vol. 2.

J. Liu et al., "Learning Human Actions Via Information Maximization," IEEE Computer Society on Computer Vision and Pattern Recognition (CVPR), Jun. 2008, 8 pages.

G.A. Cecchi et al., "Identifying Directed Links in Large Scale Functional Networks: Application to Brain fMRI," BMC Cell Biology, Jul. 2007, pp. 1-10, vol. 8, Suppl. 1.

C.-C. Chang et al., "LIBSVM: A Library for Support Vector Machines," ACM Transactions on Intelligent Systems and Technology (TIST), Apr. 2011, 39 pages, vol. 2, No. 3, Article No. 27.

* cited by examiner

METHOD AND SYSTEM FOR MODELING AND PROCESSING FMRI IMAGE DATA USING A BAG-OF-WORDS APPROACH

CROSS-REFERENCE TO RELATED APPLICATION

This application claims the benefit of U.S. Provisional Patent Application Ser. No. 61/593,946, filed on Feb. 2, 2012, the contents of which are herein incorporated by reference in their entirety.

TECHNICAL FIELD

The embodiments of the present invention relate generally to systems and methods for modeling and processing functional magnetic resonance image datasets and, more specifically, to systems and methods that can be used to perform classification of these datasets.

BACKGROUND

Recent advances in medical imaging technology have introduced functional magnetic resonance imaging (fMRI), which is capable of acquiring sequences of images of brain activity by measuring changes in blood oxygenation levels. Functional magnetic resonance imaging is increasingly used in the medical field to scan subjects, both normal and diseased. The fMRI data is a 4-dimensional dataset involving 3 spatial dimensions and one temporal dimension. fMRI has been used to study the function of brain. fMRI can give high quality visualization of location of activity within the brain, allowing for a comparison of the functions of control and disordered brains.

Brain activity can be analyzed using fMRI to diagnose disorders. For example, Attention Deficit Hyperactivity Disorder (ADHD) is one of the most commonly found behavioral disorders among children. Almost 3-5% of school aged children are diagnosed with ADHD. At present, no well-known biological measure exists to diagnose ADHD. Instead, people rely on the behavioral symptoms to identify the disorder. To understand the cause of the disorder more fundamentally, researchers are using new structural and functional imaging tools, such as fMRI.

fMRI has been used to study and diagnose different functional disorders of brain. In some analyses, task-related fMRI data is used where the test subjects perform some conscious tasks depending on the input stimuli. On the other hand, some studies use resting state brain fMRI data. Even when the brain is in the resting state, a network region, known as the default mode network (DMN) of the brain, remains active. It is believed that the DMN may be responsible for synchronizing all parts of the brain's activity; and disruptions to the network may cause a number of complex brain disorders.

Researchers have studied neural substrates relevant to ADHD related behaviors such as attention lapses, and associated the DMN as a key area for observation for a better understanding of the problem. Studies have been proposed to identify ADHD related defects. Some of the studies use group label analysis to deduce statistical differences between ADHD conditioned and control groups. Structural MRI analysis has suggested that there are abnormalities in ADHD brains, specifically in the brain areas such as frontal lobes, basal ganglia, parietal lobe, occipital lobe and cerebellum. In another set of studies, ADHD brains were analyzed using task-related fMRI data. Significantly low activity was found in the anterior cingulated cortex when ADHD subjects were asked to perform the CountingStroop during fMRI. It has also been shown that ADHD conditioned children have difficulties in performing go/nogo task and have decreased activity in frontostriatal regions, and that boys with ADHD have higher T2 relaxation time in the putamen, which is directly connected to a child's capacity to sit still.

Other work has been performed using the resting state brain fMRI to find out the abnormalities in the DMN if any. A Generalized Linear Model based regression analysis has been performed on the whole brain with respect to three frontal foci of the DMN and, which found low negative correlated activity in the precuneus/anterior cingulated cortex in ADHD subjects. Among other studies, functional abnormalities were found in the dorsal anterior cingulated cortex, and decreased regional homogeneity was shown in the frontal-striatal-cerebellar circuits, while increased regional homogeneity was shown in the occipital cortex among boys with ADHD. Decreased Amplitude of Low-frequency fluctuation (ALFF) in the right inferior frontal cortex, left sensorimotor cortex, bilateral cerebellum and the vermis was shown, as well as increased ALFF in the right anterior cingulated cortex, left sensorimotor cortex and bilateral brainstem.

While group level analysis can suggest statistical differences among two groups, it may not be useful for clinical diagnosis on an individual level. Accordingly, there is a need for methods and systems which can be used to diagnose and classify disorders, such as ADHD, on an individual level, which can connect synchronous regions of a brain.

SUMMARY

In general, exemplary embodiments of the invention include systems and methods for modeling and processing functional magnetic resonance image datasets and, in particular, systems and methods that can be used to perform classification of these datasets.

According to an exemplary embodiment of the present invention, a system for processing image data including a memory and a processor communicatively coupled to the processor comprises an imaging module capable of gathering 4-D image data from a subject, a time series module including a first extraction module capable of extracting time series data of each voxel of the subject, wherein the time series module is capable of deriving at least one feature from the time series data, a graph module including a second extraction module capable of extracting spatial and degree data of each voxel of the subject, wherein the graph module is capable of deriving at least one feature from the spatial and degree data, a combination module capable of combining the at least one feature from the time series data, and the at least one feature from the spatial and degree data to generate combined data, and a classifier capable of receiving the combined data from the combination module, and outputting a classification based on the combined data.

According to an exemplary embodiment of the present invention, a computer implemented method for processing image data, comprises gathering 4-D image data from a subject, extracting time series data, and spatial and degree data of each voxel of the subject, deriving at least one feature from the time series data, deriving at least one feature from the spatial and degree data, combining the at least one feature from the time series data, and the at least one feature from the spatial and degree data to generate combined data, and inputting the combined data to a classifier, wherein the classifier outputs a classification based on the combined data.

According to an exemplary embodiment of the present invention, an article of manufacture comprises a non-transitory computer readable storage medium comprising program code tangibly embodied thereon, which when executed by a computer, performs method steps for processing image data, the method steps comprising gathering 4-D image data from a subject, extracting time series data, and spatial and degree data of each voxel of the subject, deriving at least one feature from the time series data, deriving at least one feature from the spatial and degree data, combining the at least one feature from the time series data, and the at least one feature from the spatial and degree data to generate combined data, and inputting the combined data to a classifier, wherein the classifier outputs a classification based on the combined data.

According to an exemplary embodiment of the present invention, an apparatus for processing image data, comprises a memory, and a processor coupled to the memory and configured to execute code stored in the memory for gathering 4-D image data from a subject, extracting time series data, and spatial and degree data of each voxel of the subject, deriving at least one feature from the time series data, deriving at least one feature from the spatial and degree data, combining the at least one feature from the time series data, and the at least one feature from the spatial and degree data to generate combined data, and inputting the combined data to a classifier, wherein the classifier outputs a classification based on the combined data.

These and other exemplary embodiments of the invention will be described or become apparent from the following detailed description of exemplary embodiments, which is to be read in connection with the accompanying drawings.

BRIEF DESCRIPTION OF THE DRAWINGS

Exemplary embodiments of the present invention will be described below in more detail, with reference to the accompanying drawings, of which.

DETAILED DESCRIPTION OF EXEMPLARY EMBODIMENTS

Figure 1:
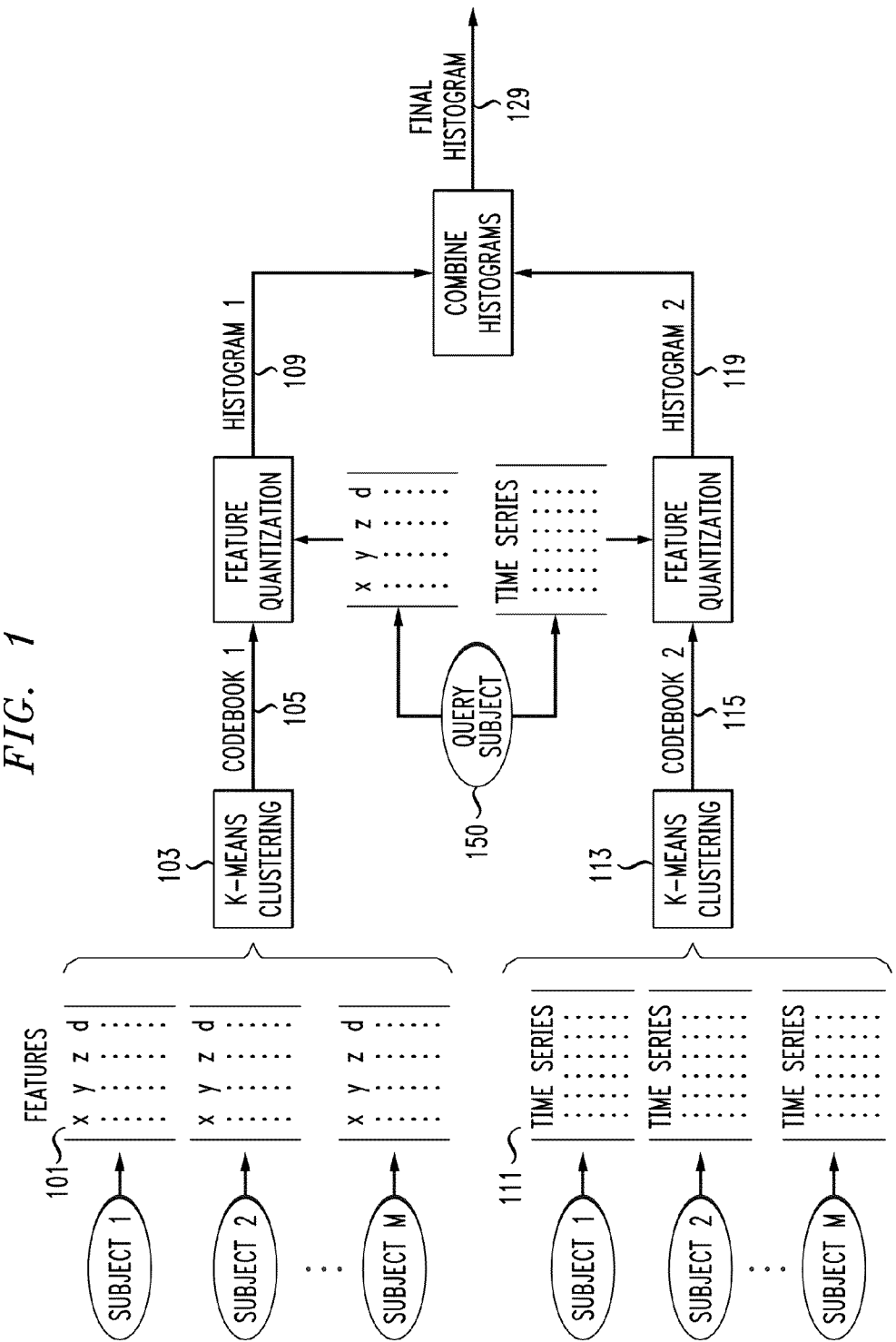
FIG. 1 is a high level diagram of a method for modeling and processing functional magnetic resonance image datasets according to an exemplary embodiment of the invention.

Exemplary embodiments of the invention will now be discussed in further detail with regard to systems and methods for modeling and processing functional magnetic resonance image datasets and, in particular, to systems and methods that can be used to perform classification of these datasets. This invention may, however, be embodied in many different forms and should not be construed as limited to the embodiments set forth herein.

Embodiments of the present invention provide methods and systems for diagnosing normal and diseased subjects possessing a disease or disorder through functional magnetic resonance imaging (fMRI). While the disclosure includes the application of the embodiments to Attention Deficit Hyperactivity Disorder (ADHD), the embodiments of the present invention are not limited to the application to ADHD, and may be applied to any suitable situation where fMRI analysis is used, such as, for example, in connection with other brain disorders or diseases, or disorders or diseases occurring in other parts of the body which are scanned and imaged using fMRI, or any type of data analysis where data including spatial and time elements is analyzed.

ADHD is an example of a brain disorder where not much information is known about the cause of the disorder. Embodiments of the present invention provide a method for automatic classification of ADHD subjects, or of subjects having another disorder, and normal controls using fMRI studies of the resting state brain. Embodiments of the present invention use resting state brain fMRI data and hypothesize that the difference of ADHD conditioned and control brains lies in the variation of DMN structural connections. Given a set of fMRI scans, and training examples, embodiments of the present invention are applied to classify individual scans into distinct classes (e.g., disease vs. non-disease).

Some fMRI techniques work with block-design data (i.e., stimulus is turned on and off in blocks, with a block representing a certain period of time, e.g., 10 seconds). However, for diagnosing certain conditions like ADHD, the resting state of the brain is important. When analyzing the resting state of the brain, a specific stimulus cannot be used, and hence the block-design method for analysis is not applicable. For instance, the general linear model, known as GLM, is not applicable to resting state data. In such cases, network analysis can be helpful, which turns the fMRI data into a graph regardless of the experimental protocol used (e.g., block-design or resting-state). However, network analysis by itself ignores the information present in the spatio-temporal time signatures of different subjects. Hence, embodiments of the present invention combine the features in the spatio-temporal time series data with network-derived features. In other words, in accordance with embodiments of the present invention, features in two complementary domains, the time domain and the graph/spatial domain, are combined.

In accordance with embodiments of the present invention, fMRI data can be viewed as 4-D video such that the 3-D volume of brain is divided into small voxels and imaged for a certain duration. In other words, each voxel, which is a volumetric picture element, is imaged for a predetermined period of time, such as, for example, 20-30 minutes. As a result, the time-series of intensity values are provided for each voxel. The correlation of these intensity time-series can be an indication of how synchronous the activities of two voxels are, and higher correlation values suggest that two voxels are working in synchronization. By computing correlations for all or a predetermined number of possible voxel pairs within a subject and establishing the connections between the voxel pairs based on high correlation values, a functional network structure can be generated for each brain. The resulting network structure may be indicative of a condition that is present (or not present) in the brain being analyzed. For example, in the case of ADHD, a network structure may show a lack of connection between the frontal and posterior regions of the brain.

According to embodiments of the present invention, correlation measures between voxels can be computed by a comparison of time traces of each voxel. If, for example, compared voxels have similar time traces, a connection between the voxels can be concluded. According to embodiments of the present invention, a high correlation value may be a value exceeding a predetermined threshold. For example, if correlation values are between 0 and 1, correlation values greater than or equal to 0.7 may be considered high correlation values.

In accordance with embodiments of the present invention, a bag-of-words (BoW) approach is used to capture the network features, such as degree of connectivity of each voxel, and to represent each network by a histogram. First used in natural language processing, the BoW approach allows a dictionary-based modeling of documents, and each document looks like a bag, which contains some words from the dictionary. This type of approach has also been applied in the computer vision area and to image or video representation. When applied to document classification, a BoW is a sparse vector of occurrence counts of words, or a sparse histogram over the vocabulary. When applied to image classification, image features are treated as words, so that the BoW for images is a sparse vector of occurrence counts of image features, or a sparse histogram over the vocabulary of image features.

Network features and raw intensity time-series of the voxels can be clustered and represented as histograms using the BoW approach. In accordance with embodiments of the invention, experimental results verified that using a combination of network features and raw intensity time-series histograms results in a better classification accuracy. These histograms can be fed to a support vector machine (SVM) for automatic classification of ADHD.

Embodiments of the present invention provide techniques that combine feature representations from the time series with network-related spatial features, by for example, combining a BoW approach for feature extraction with network features, such as degree and cycle maps.

In accordance with embodiments of the present invention, the correlation between every possible voxel pair within a subject is computed and a network based on the high correlation values is constructed. The BoW approach is used to represent each subject as a histogram of network features; such as number of degrees per voxel or number of k-length cycles for voxel pairs. According to an embodiment, the classification is done using, for example, an SVM.

Referring to FIG. 1, embodiments of the present invention apply the BoW approach to biomedical imaging, specifically for processing the functional brain networks, to combine the temporal and graph/spatial domains. Following the BoW representation, each subject is treated as a document. Features, which can be considered as words, are extracted from each voxel of the resting state fMRI scans of these subjects. Codebooks for each domain are generated using, for example, K-means clustering algorithm(s), or other appropriate algorithm or clustering technique. After the generation of the codebooks, each subject is represented with histograms based on network features.

Specifically, referring to FIG. 1, codebook 1 (105) is derived from [x, y, z, d] vectors, which are 4-tuple feature vectors representing the spatial locations of each voxel (x, y, z) and the degree of each voxel (d). The degree of a voxel is the number of edges that emanate from the voxel; in other words, the number of voxels to which a given voxel is connected. 3-D degree maps are computed for each voxel of each subject 1, 2, ... M, which show how many voxels a given voxel is connected to. The value of the degree map at voxel i is the number of voxels that voxel i is connected to. The feature vector is a 4-tuple vector [x, y, z, d], which includes the 3-D spatial coordinates of a voxel and its degree that is defined by the degree map.

The [x, y, z, d] data for each voxel of each subject 1, 2, ... M, as shown by matrices 101, is applied to the K-means clustering algorithm 103 to result in codebook 1 (105). According to an embodiment, the data can be normalized to have values between 0 and 1 prior to clustering. For generating the codebook for the BoW approach, K-means clustering (K=100) of the 4-tuples across all the subjects can be performed to obtain the cluster centers, which form histogram bins. The number of the clusters is the codebook size. According to an embodiment, each 4-tuple feature of a subject is mapped to a certain cluster center, which may be the nearest neighbor of that feature. All features of a subject being mapped to the cluster centers, the subject can be represented by a histogram of the codewords.

Codebook 1 (105) includes a representative of the most frequently occurring 4-tuple feature vectors from the data inputted to the K-means clustering algorithm 103. New data sets can be described in terms of codebook 1 (105). For example, a new data set may be said to include, for example, feature vector 1 including a set of values $[x_1, y_1, z_1, d_1]$ and feature vector 10 including another set of values $[x_{10}, y_{10}, z_{10}, d_{10}]$, etc. of codebook 1. The data from codebook 1 (105) is tabulated into histogram 1 (109) which graphs the frequency of occurrence of the feature vectors (e.g., codewords) from codebook 1.

Figure 2:
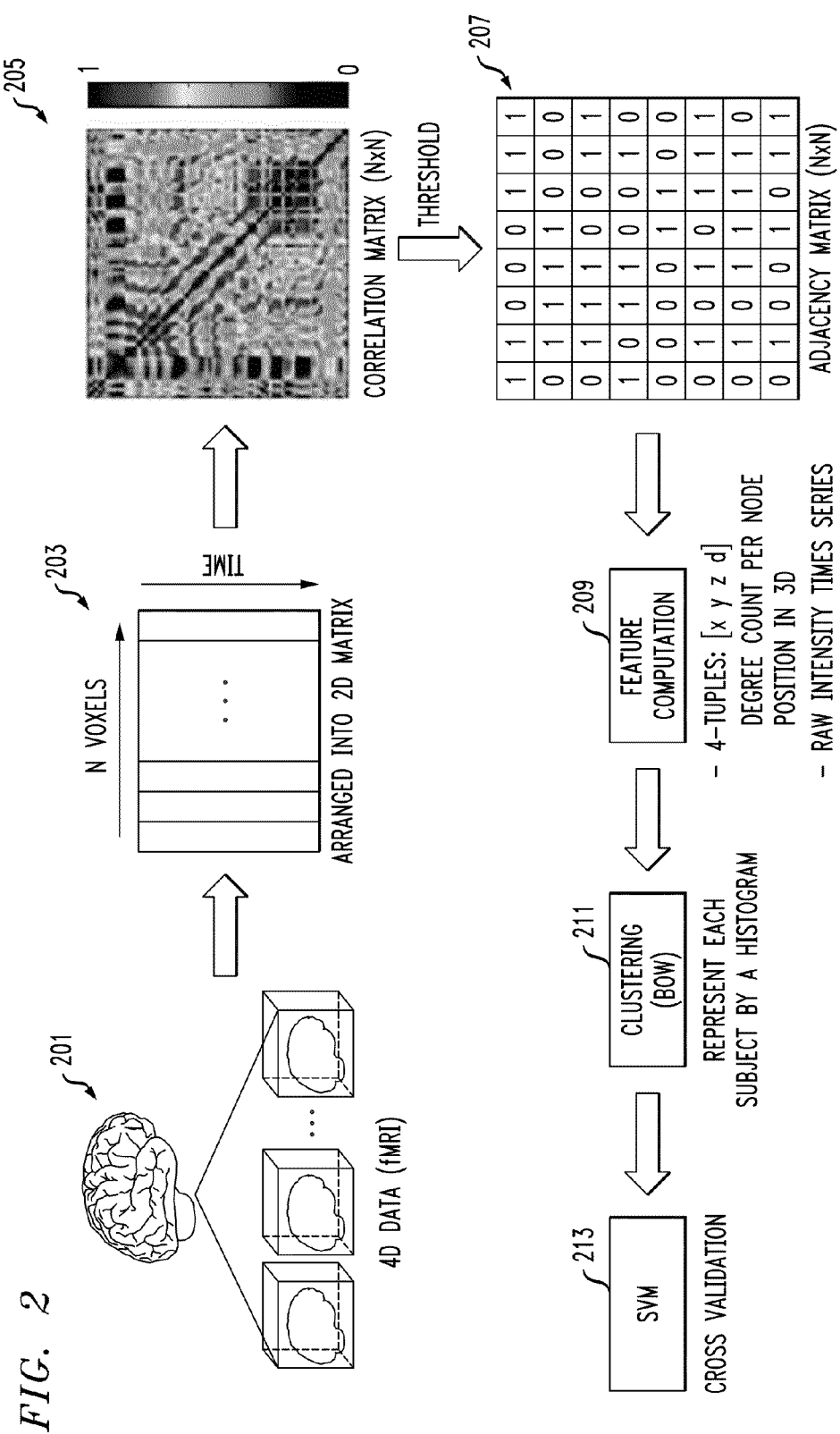
FIG. 2 is a high level diagram of a method for modeling and processing functional magnetic resonance image datasets according to an exemplary embodiment of the invention.

The fMRI scan of a subject consists of a number of intensity values. Therefore, in accordance with embodiments of the present invention, the BoW approach is also applied to time series data of raw intensity values. Following the same or similar steps as with the network features, another codebook of elements (e.g., 75 elements) is generated and each subject is represented by a histogram having a number of bins corresponding to the number elements (e.g., 75 bins). More specifically, codebook 2 (115) is derived from the correlations of the time series between each voxel of each subject. Referring to FIG. 2, for each subject, the time series of each voxel within an anatomical brain/skull mask 201 is extracted. The time series is a variation in the strength of a voxel over a period of time. A 2D matrix 203 is generated showing the time series for N voxels.

From the 4-D fMRI data, a correlation is computed between each set of two voxels in a subject. For any two voxels, if the time series are u and v respectively, the correlation can be computed by:

$$r = \frac{\left(T \sum_{i=1}^{T} u_i v_i\right) - \left(\sum_{i=1}^{T} u_i\right)\left(\sum_{i=1}^{T} v_i\right)}{\sqrt{\left[T \sum_{i=1}^{T} u_i^2 - \left(\sum_{i=1}^{T} u_i\right)^2\right]\left[T \sum_{i=1}^{T} v_i^2 - \left(\sum_{i=1}^{T} v_i\right)^2\right]}}, \quad (1)$$

where T is the length of the time series.

The correlations are plotted in a correlation map 205 having size N×N for each subject, where N is the number of voxels inside the anatomical brain mask for each subject. Each block of the N×N matrix includes the pairwise correlation coefficient (γ) from equation (1) for each voxel pair, where an ith row of the matrix corresponds to the pairwise correlation values of the ith voxel with all other voxels within the subject. Then, according to an embodiment, an adjacency matrix 207 of the voxels is computed by thresholding the high correlation values, wherein the high correlation values are set to one and the rest of the entries set to zero. The ith voxel is deemed to be connected to all the voxels for which non-zero values are present in the ith row of the adjacency matrix. According to an embodiment, a high correlation value is a value of $\gamma$ exceeding a predetermined threshold. In the case where the values of $\gamma$ are normalized to between 0 and 1, a high correlation may be, for example, a value greater than or equal to 0.7.

Referring back to FIG. 1, the adjacency matrices 207 of each subject 1, 2, ... M (represented by 111 in FIG. 1) are applied to the K-means clustering algorithm 113 to result in codebook 2 (115). Codebook 2 (115) includes a representative of the most frequently occurring and/or high correlations from the data inputted to the K-means clustering algorithm 113. For example, voxel time series that look similar will be grouped together in a cluster and will form a word. The data from codebook 2 (115) is tabulated into histogram 2 (119) which graphs the frequency of occurrence of the correlations (e.g., codewords) from codebook 2.

According to an embodiment, a training or learning mode is performed where histograms 1 and 2 (109, 119) and combined histograms 129 are created from subjects 1, 2, ... M for training an SVM classifier. Representation of each subject as a histogram using the BoW approach, allows for use of any discriminative classification algorithm, such as what would be included in an SVM. By normalizing and concatenating the two computed histograms for each subject as the final feature vector (e.g., 175 dimensions), an SVM is trained for classification of ADHD conditioned and control subjects. Referring to FIG. 1, once the SVM classifier is trained, spatial, degree and time series data is taken from a query subject 150 (e.g., a subject for which the presence of a disorder (such as ADHD) is to be tested). The data from the query subject is quantized at blocks 107 and 117, where features are clustered using, for example, K-means clustering, and histograms 1 and 2 (109, 119), and combined histogram 129 are generated for the query subject 150. The resulting data from the histograms 1 and 2 (109, 119) and combined histogram 129 for the query subject 150 are input to an SVM for classification.

Referring back to FIG. 2, blocks 209 and 211 represent the quantization of the 4-tuple [x, y, z, d] feature vector data and raw intensity time series data for each voxel of a subject, where features are clustered and the histograms 109, 119 and 129 are generated, and block 213 represents input of the resulting data to an SVM for classification.

Figure 5:
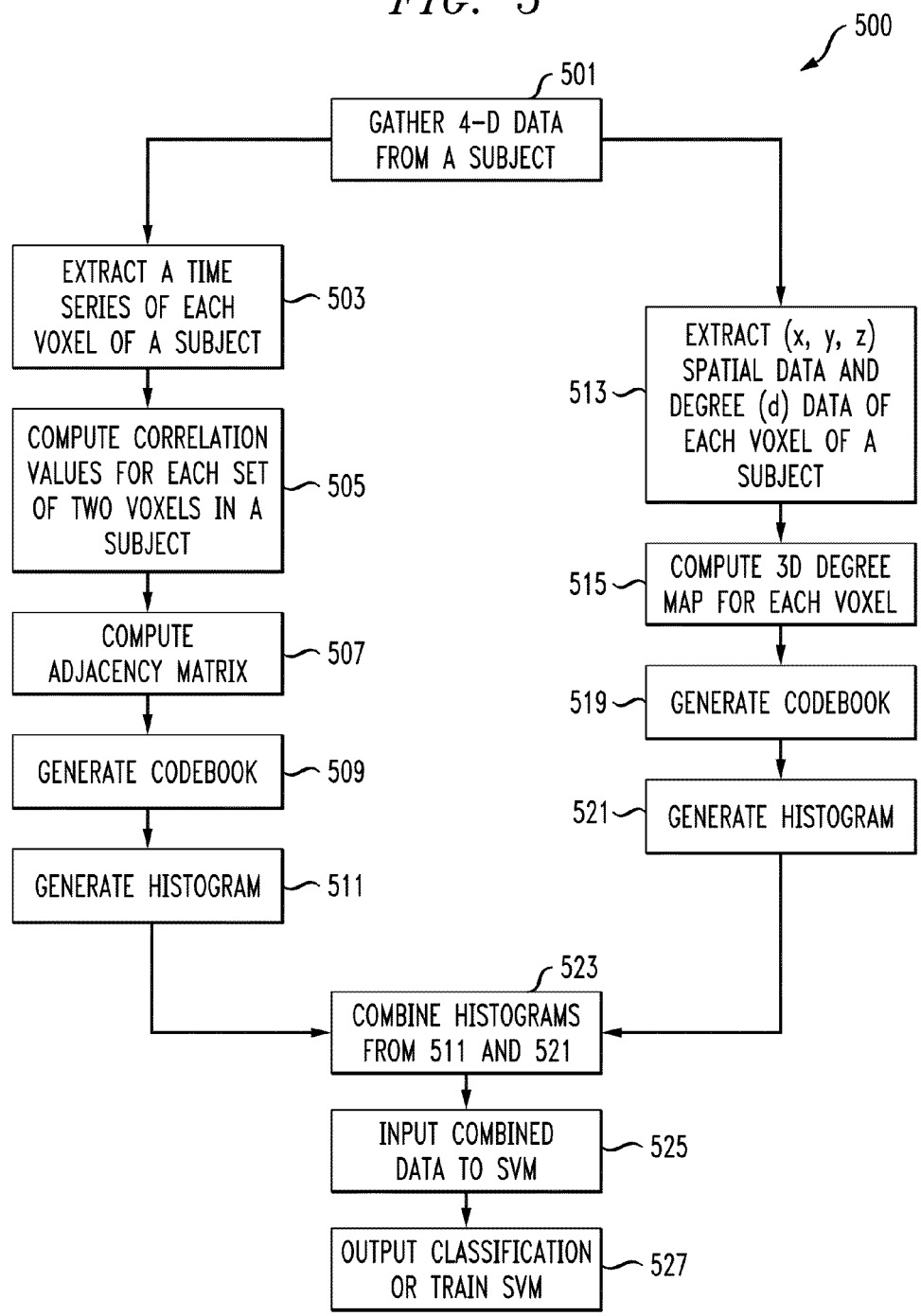
FIG. 5 is a flow diagram of a method for modeling and processing functional magnetic resonance image datasets according to an exemplary embodiment of the invention.

Referring to FIG. 5, a method 500 for modeling and processing functional magnetic resonance image datasets according to an embodiment of the present invention comprises gathering 4-D data from a subject, such as, for example, 4-D fMRI data from an anatomical brain/skull mask of a subject (block 501). At block 503, a time series of each voxel of a subject is extracted, and at block 505 correlation values for each set of two voxels in a subject are computed in accordance with equation (1). Then, at block 507, an adjacency matrix is computed by thresholding the high correlation values, and at block 509, a codebook based on the correlation values and/or adjacency matrix is generated using a K-means clustering algorithm. After the generation of the codebook, a histogram based on the codebook from block 509 is generated at block 511.

At block 513, (x, y, z) spatial data and degree (d) data for each voxel of a subject is extracted, and at block 515 a 3-D degree map is computed for each voxel. Then, at block 519, a codebook based on the [x, y, z, d] feature vectors and/or the 3-D degree map is generated using a K-means clustering algorithm. After the generation of the codebook, a histogram based on the codebook from block 519 is generated at block 521. The histograms from blocks 511 and 521 are combined at block 523 to generate a combined histogram. At block 525, the combined data is input to an SVM. At block 527, the SVM outputs a classification based on the combined data, or, if in a training/learning mode, the SVM is trained with the combined data.

Figure 6:
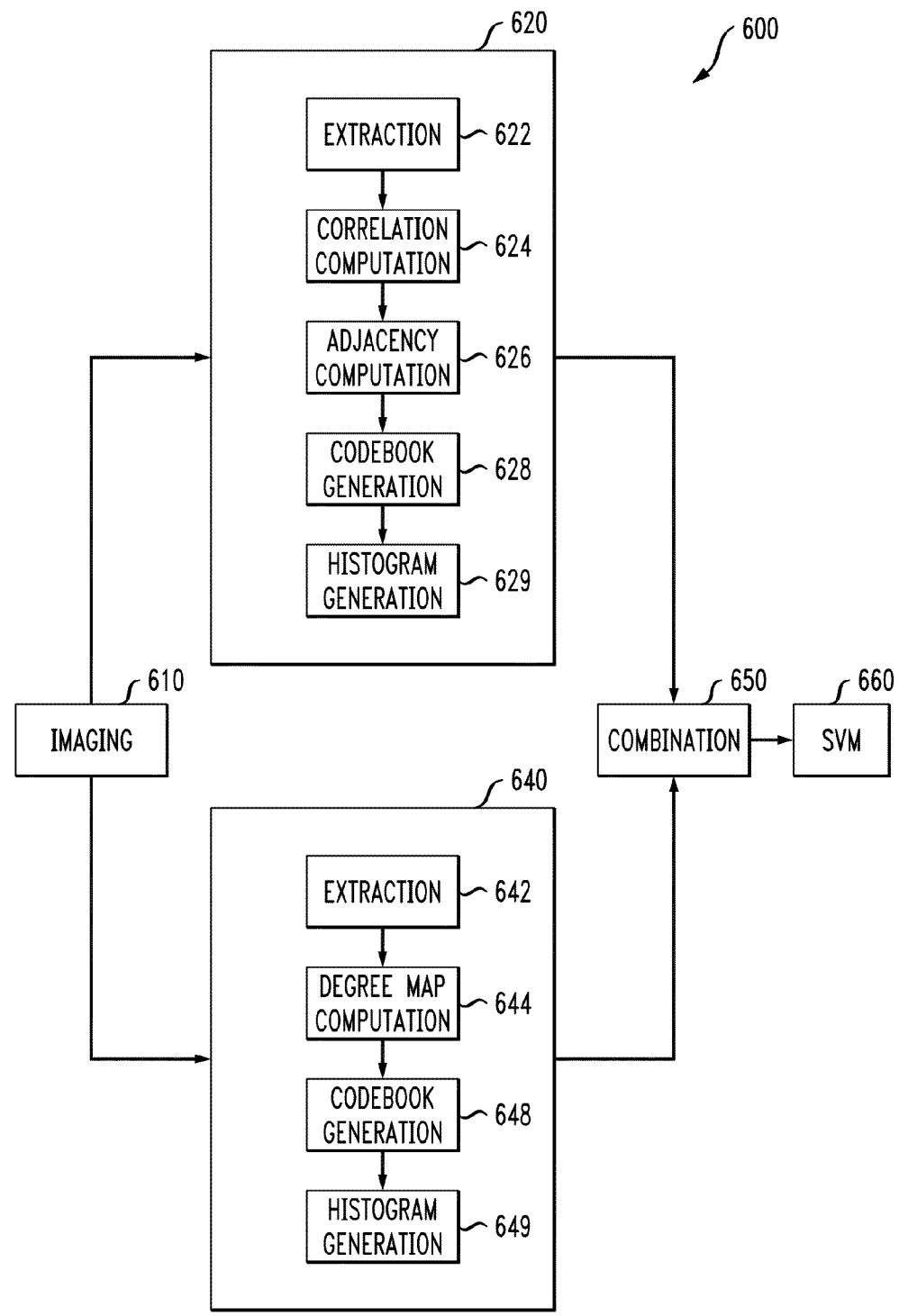
FIG. 6 is a high-level diagram of a system for modeling and processing functional magnetic resonance image datasets according to an exemplary embodiment of the invention.

Referring to FIG. 6, a system 600 for modeling and processing functional magnetic resonance image datasets, according to an embodiment of the present invention, comprises an imaging module 610, which gathers 4-D data from a subject. The imaging module 610 can be, for example, an fMRI apparatus which collects 4-D fMRI data from an anatomical brain/skull mask of a subject. The imaging module 610 outputs the collected 4-D data to a time series module 620 and to a graph module 640. The time series module 620 includes an extraction module 622 which extracts a time series of each voxel of a subject, and a correlation computation module 624 which receives the time series data from the extraction module 622, and computes correlation values for each set of two voxels in a subject in accordance with equation (1). An adjacency computation module 626 receives the correlation values from the correlation computation module 624, and computes an adjacency matrix by thresholding the high correlation values from the correlation computation module 624. A codebook generation module 628 generates a codebook based on the correlation data from the adjacency computation module 626 using a K-means clustering algorithm. The histogram generation module 629 generates a histogram based on the codebook from the codebook generation module 628.

The graph module 640 includes an extraction module 642 which extracts (x, y, z) spatial data and degree (d) data for each voxel of a subject, and degree map computation module 644, which computes a 3-D degree map for each voxel from the spatial and degree data received from the extraction module 642. A codebook generation module 648 generates a codebook based on the [x, y, z, d] feature vectors from the extraction module 642, and/or the 3-D degree map from the degree map computation module 644, using a K-means clustering algorithm. The histogram generation module 649 generates a histogram based on the codebook from the codebook generation module 648. The histograms from the histogram generation modules 629 and 649 are combined by the combination module 650 to generate a combined histogram. The combined data is input to a classifier, such as SVM 660. The SVM 660 outputs a classification based on the combined data, or, if in a training/learning mode, the SVM 660 is trained with the combined data.

Experimental Example 1

In experimental example 1, using the degree map feature without combining the time series data, 83 ADHD subjects from the Kennedy Krieger Institute (KKI) Center for Development and Learning ("KKI Center") ADHD-200 Global Competition Test Dataset were tested. Preprocessed fMRI data, which was written into Montreal Neurological Institute (MNI) space at 4 mm×4 mm×4 mm voxel resolution, nuisance variance removed, filtered using a bandpass filter (0.009 Hz<f<0.08 Hz) and blurred with a 6-mm full width at half maximum (FWHM) Gaussian filter, was provided by NITRC ADHD 1000 connectome project organizer.

Figure 3:
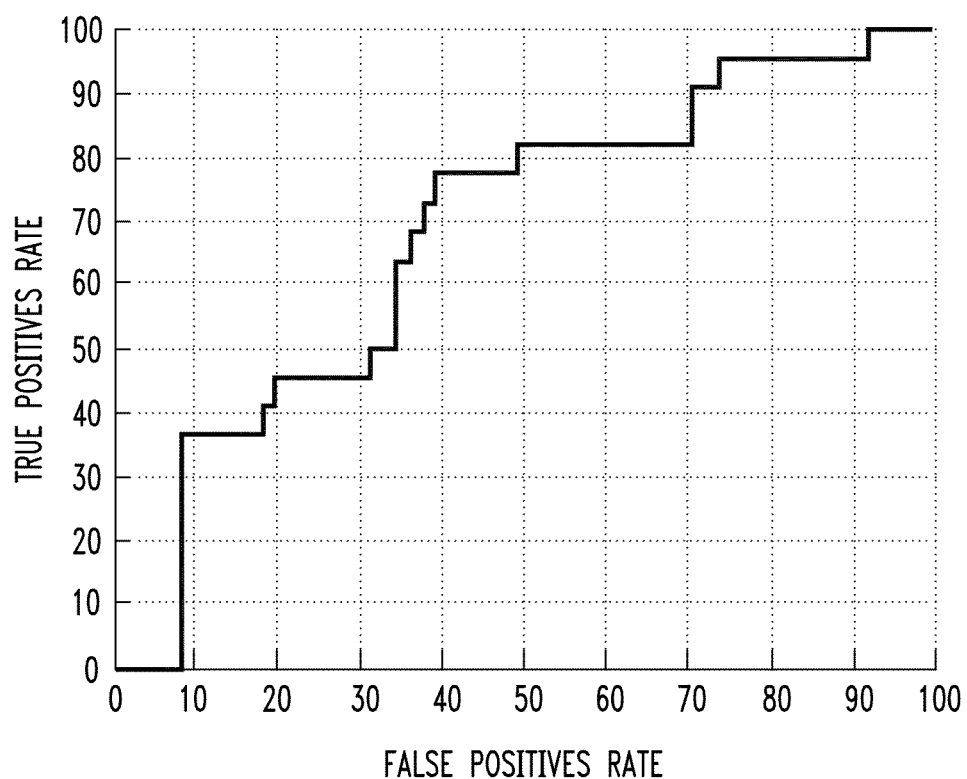
FIG. 3 is a graph of receiver operating characteristics for experimental example 1 using a degree map without combining time series data.

In the sample set, 22 subjects were diagnosed with ADHD and 61 subjects were diagnosed as not having ADHD. In the experimental example, leave-one-out cross-validation was performed, in which a single subject from the dataset is used for testing (e.g., query subject), and the remaining subjects are used for training an SVM classifier. Repeating this process as many times as the number of subjects; each subject in the dataset was used once as the validation data, and a classification accuracy of 65% (78% true positive and 39% false positive rate) was obtained. The Receiver Operating Characteristics (ROC) of experimental example 1 are shown in FIG. 3.

Experimental Example 2

For the comparison of classification accuracies using network features, raw intensity time series and the combined features, experimental example 2 applied embodiments of the present invention to a larger subset of the ADHD-200 Global Competition Test Dataset, including 506 subjects. A description of the included subjects in this experimental example is shown in Table 1 below.

TABLE 1

Description of the test subjects of the larger dataset.

| Test Center | Number of Subjects | Number of ADHD conditioned subjects | Number of control subjects | Female | Male |
|---|---|---|---|---|---|
| KKI | 83 | 22 | 61 | 37 | 46 |
| Neuro Image | 48 | 25 | 23 | 17 | 31 |
| NYU part 1 | 55 | 31 | 24 | 19 | 36 |
| NYU part 2 | 67 | 32 | 35 | 22 | 45 |
| OHSU | 79 | 37 | 42 | 36 | 43 |
| Peking 1 | 85 | 24 | 61 | 49 | 36 |
| Pittsburgh | 89 | 0 | 89 | 43 | 46 |

Figure 4:
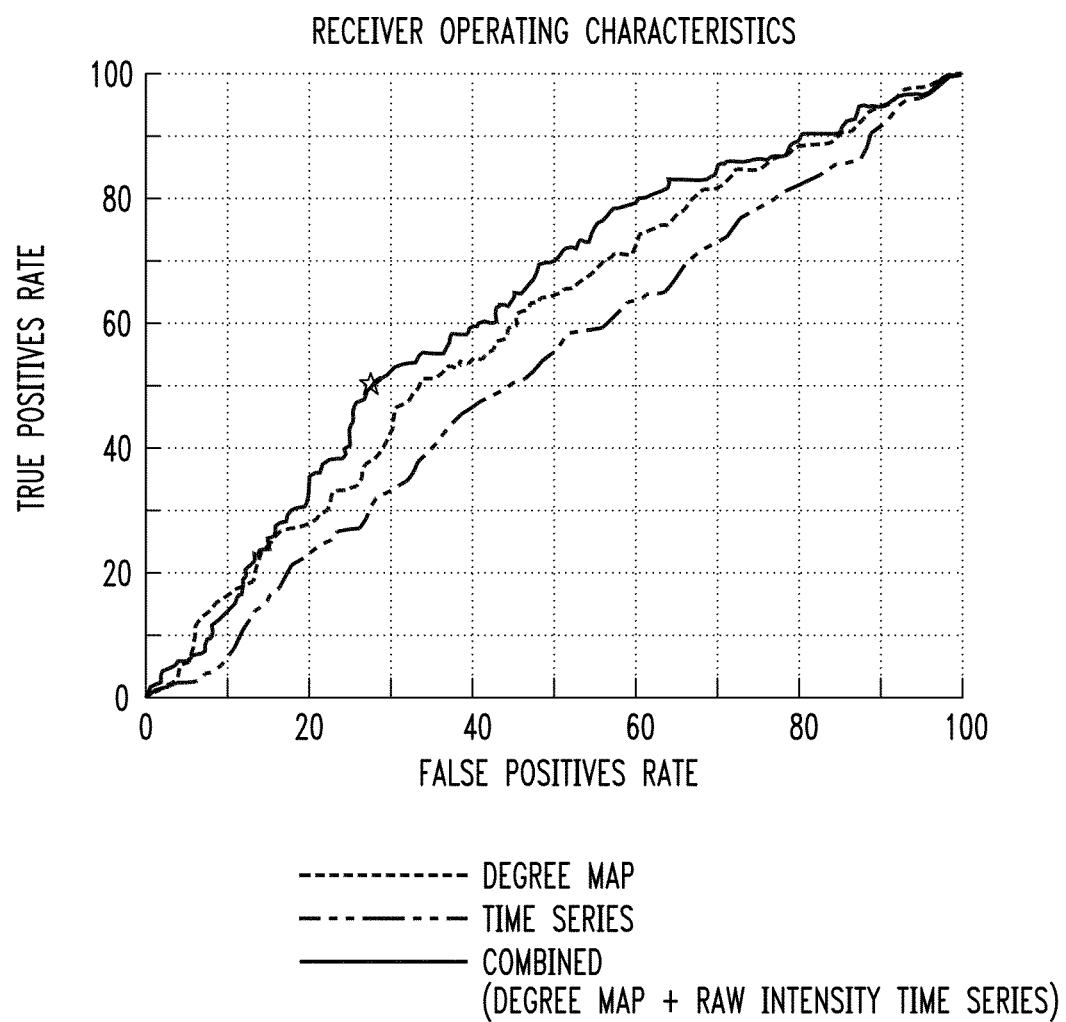
FIG. 4 is a graph of a comparison of receiver operating characteristics for experimental example 2, comparing receiver operating characteristics for the combination of the degree map and the raw intensity time series in accordance with an embodiment of the present invention, with receiver operating characteristics for the degree map and time series alone.

Using the dataset of 506 subjects resulted in 64% overall detection at the cost of 50% true positives and 72% true negatives, as depicted in FIG. 4 illustrating receiver operating characteristics curves for different combinations of features on 506 subjects. As can be seen from FIG. 4, the combined data exhibits overall higher true positive rates for given false positive rates than both the degree map and time series alone. Accordingly, the combination of the degree map and the raw intensity time series results in higher classification accuracy than the degree map and time series alone. The classification accuracies for both experimental examples are illustrated in Table 2 below.

TABLE 2

Results for ADHD classification.

| Used Feature | Number of Subjects | Accuracy |
|---|---|---|
| Degree Map | 83 | 65% |
| Degree Map | 506 | 61% |
| Raw Intensity Time Series | 506 | 56% |
| Degree Map + Raw Intensity Time Series | 506 | 64% |

As will be appreciated by one skilled in the art, aspects of the present invention may be embodied as a system, apparatus, method, or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

FIGS. 1-6 illustrate the architecture, functionality, and operation of possible implementations of systems, methods, and computer program products according to various embodiments of the present invention. In this regard, each block in a flowchart or a block diagram may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagram and/or flowchart illustration, and combinations of blocks in the block diagram and/or flowchart illustration, can be implemented by special purpose hardware-based systems that perform the specified functions or acts, or combinations of special purpose hardware and computer instructions.

Figure 7:
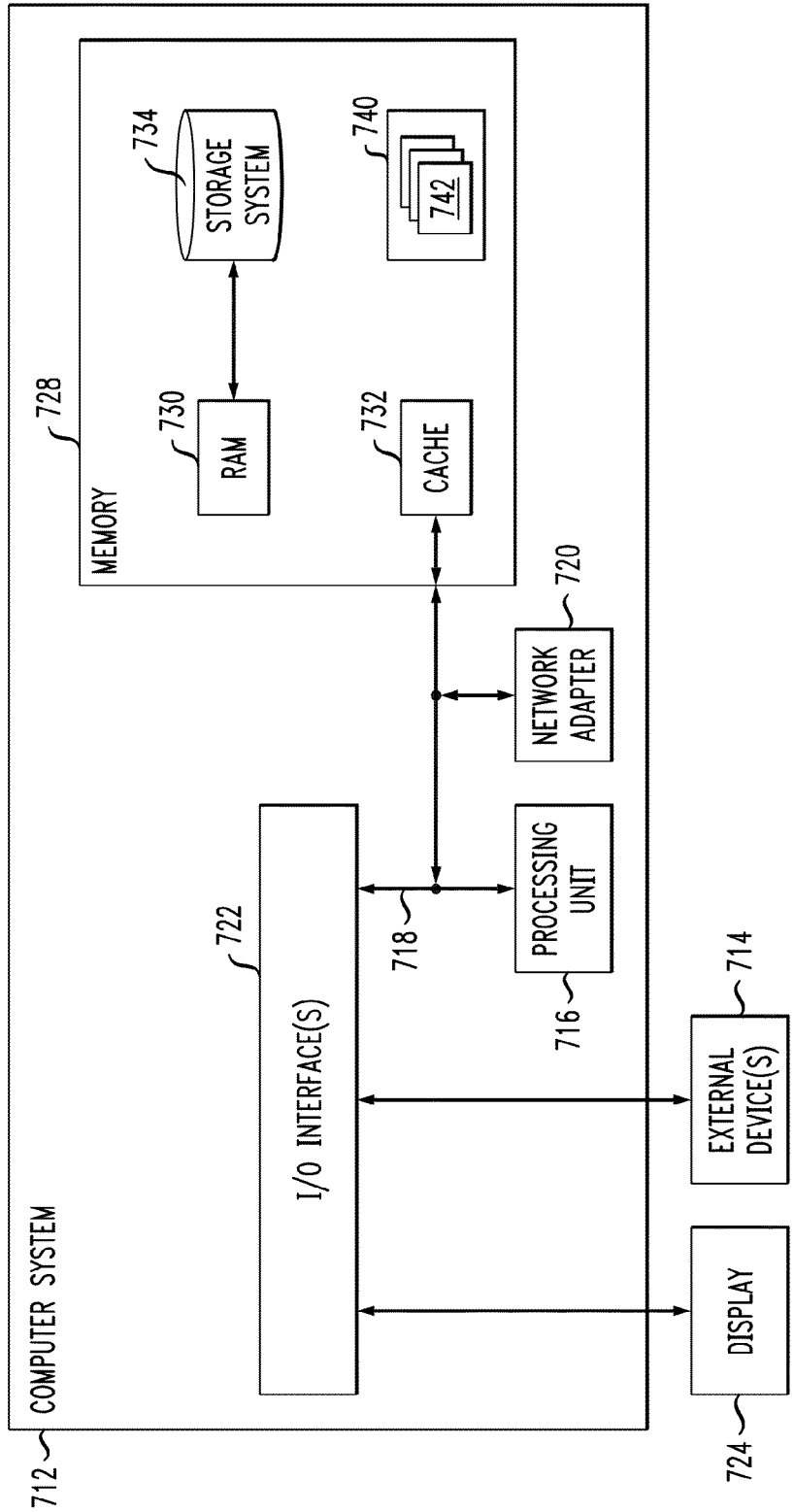
FIG. 7 illustrates a computer system in accordance with which one or more components/steps of the techniques of the invention may be implemented, according to an exemplary embodiment of the invention.

One or more embodiments can make use of software running on a general-purpose computer or workstation. With reference to FIG. 7, in a computing node 710 there is a computer system/server 712, which is operational with numerous other general purpose or special purpose computing system environments or configurations. Examples of well-known computing systems, environments, and/or configurations that may be suitable for use with computer system/server 712 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 712 may be described in the general context of computer system executable instructions, such as program modules, being executed by a computer system. Generally, program modules may include routines, programs, objects, components, logic, data structures, and so on that perform particular tasks or implement particular abstract data types. Computer system/server 712 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 7, computer system/server 712 in computing node 710 is shown in the form of a general-purpose computing device. The components of computer system/server 712 may include, but are not limited to, one or more processors or processing units 716, a system memory 728, and a bus 718 that couples various system components including system memory 728 to processor 716.

The bus 718 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

The computer system/server 712 typically includes a variety of computer system readable media. Such media may be any available media that is accessible by computer system/server 712, and it includes both volatile and non-volatile media, removable and non-removable media.

The system memory 728 can include computer system readable media in the form of volatile memory, such as random access memory (RAM) 730 and/or cache memory 732. The computer system/server 712 may further include other removable/non-removable, volatile/nonvolatile computer system storage media. By way of example only, storage system 734 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to the bus 718 by one or more data media interfaces. As depicted and described herein, the memory 728 may include at least one program product having a set (e.g., at least one) of program modules that are configured to carry out the functions of embodiments of the invention. A program/utility 740, having a set (at least one) of program modules 742, may be stored in memory 728 by way of example, and not limitation, as well as an operating system, one or more application programs, other program modules, and program data. Each of the operating system, one or more application programs, other program modules, and program data or some combination thereof, may include an implementation of a networking environment. Program modules 742 generally carry out the functions and/or methodologies of embodiments of the invention as described herein.

Computer system/server 712 may also communicate with one or more external devices 714 such as a keyboard, a pointing device, a display 724, etc., one or more devices that enable a user to interact with computer system/server 712, and/or any devices (e.g., network card, modem, etc.) that enable computer system/server 712 to communicate with one or more other computing devices. Such communication can occur via Input/Output (I/O) interfaces 722. Still yet, computer system/server 712 can communicate with one or more networks such as a local area network (LAN), a general wide area network (WAN), and/or a public network (e.g., the Internet) via network adapter 720. As depicted, network adapter 720 communicates with the other components of computer system/server 712 via bus 718. It should be understood that although not shown, other hardware and/or software components could be used in conjunction with computer system/server 712. Examples, include, but are not limited to: microcode, device drivers, redundant processing units, external disk drive arrays, RAID systems, tape drives, and data archival storage systems, etc.

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

We claim:

1. A system for processing image data including a memory and a processor communicatively coupled to the processor, comprising:
    an imaging module capable of gathering four-dimensional image data from a subject;
    a time series module including a first extraction module capable of extracting time series data of each voxel of the subject, wherein the time series module is capable of deriving at least one feature from the time series data;
    a graph module including a second extraction module capable of extracting spatial and degree data of each voxel of the subject, wherein the graph module is capable of deriving at least one feature from the spatial and degree data;
    a combination module capable of combining the at least one feature from the time series data, and the at least one feature from the spatial and degree data to generate combined data; and
    a classifier capable of receiving the combined data from the combination module, and outputting a classification based on the combined data.

2. The system of claim 1, wherein the time series module further includes:
    a correlation computation module capable of computing correlation values for each set of two voxels in the subject; and
    an adjacency computation module capable of computing an adjacency matrix from the correlation values.

3. The system of claim 2, wherein the correlation computation module computes the correlation values by equation:

$$r = \frac{\left(T\sum_{i=1}^{T} u_i v_i\right) - \left(\sum_{i=1}^{T} u_i\right)\left(\sum_{i=1}^{T} v_i\right)}{\sqrt{\left[T\sum_{i=1}^{T} u_i^2 - \left(\sum_{i=1}^{T} u_i\right)^2\right]\left[T\sum_{i=1}^{T} v_i^2 - \left(\sum_{i=1}^{T} v_i\right)^2\right]}}$$

where u and v are the time series for any two voxels, and T is a length of the time series.

4. The system of claim 2, wherein the adjacency computation module computes the adjacency matrix by thresholding the correlation values exceeding a predetermined value.

5. The system of claim 4, wherein the adjacency computation module sets the correlation values exceeding the predetermined value to one and remaining correlation values to zero.

6. The system of claim 2, wherein the time series module further includes:
    a codebook generation module capable of generating a codebook based on the adjacency matrix; and
    a histogram generation module capable of generating a histogram based on the codebook.

7. The system of claim 1, wherein the graph module further includes a degree map computation module capable of computing a three-dimensional degree map for each voxel.

8. The system of claim 7, wherein the graph module further includes:
    a codebook generation module capable of generating a codebook based on the three-dimensional degree map; and
    a histogram generation module capable of generating a histogram based on the codebook.

9. The system of claim 1, wherein the combination module is capable of combining a first histogram generated from a first codebook based on an adjacency matrix with a second histogram generated from a second codebook based on a three-dimensional degree map, to form a combined histogram.

10. The system of claim 1, wherein the time series and graph modules respectively use a K-means clustering algorithm to derive the at least one feature from the time series data and the at least one feature from the spatial and degree data.

11. The system of claim 1, wherein the spatial data comprises x, y and z coordinates of each voxel and the degree data comprises a number of voxels to which each voxel is connected.

12. A computer implemented method for processing image data, the method comprising:
    gathering four-dimensional image data from a subject;
    extracting time series data, and spatial and degree data of each voxel of the subject;
    deriving at least one feature from the time series data;
    deriving at least one feature from the spatial and degree data;
    combining the at least one feature from the time series data, and the at least one feature from the spatial and degree data to generate combined data; and
    inputting the combined data to a classifier, wherein the classifier outputs a classification based on the combined data.

13. The method of claim 12, wherein deriving the at least one feature from the time series data comprises:
    computing correlation values for each set of two voxels in the subject; and
    computing an adjacency matrix from the correlation values.

14. The method of claim 13, wherein the correlation values are computed by equation:

$$r = \frac{\left(T\sum_{i=1}^{T} u_i v_i\right) - \left(\sum_{i=1}^{T} u_i\right)\left(\sum_{i=1}^{T} v_i\right)}{\sqrt{\left[T\sum_{i=1}^{T} u_i^2 - \left(\sum_{i=1}^{T} u_i\right)^2\right]\left[T\sum_{i=1}^{T} v_i^2 - \left(\sum_{i=1}^{T} v_i\right)^2\right]}}$$

where u and v are the time series for any two voxels, and T is a length of the time series.

15. The method of claim 13, wherein the adjacency matrix is computed by thresholding the correlation values exceeding a predetermined value.

16. The method of claim 15, wherein the correlation values exceeding the predetermined value are set to one and remaining correlation values are set to zero.

17. The method of claim 13, wherein deriving the at least one feature from the time series data further comprises generating a codebook based on the adjacency matrix, and a histogram based on the codebook.

18. The method of claim 12, wherein deriving the at least one feature from the spatial and degree data comprises computing a three-dimensional degree map for each voxel.

19. The method of claim 18, wherein deriving the at least one feature from the spatial and degree data further comprises generating a codebook based on the three-dimensional degree map, and a histogram based on the codebook.

20. The method of claim 12, wherein combining the at least one feature from the time series data, and the at least one feature from the spatial and degree data to generate combined data comprises combining a first histogram generated from a first codebook based on an adjacency matrix with a second histogram generated from a second codebook based on a three-dimensional degree map, to form a combined histogram.

21. The method of claim 12, wherein the image data is four-dimensional fMRI data from an anatomical brain mask of the subject.

22. The method of claim 12, wherein deriving the at least one feature from the time series data and deriving the at least one feature from the spatial and degree data is performed using a K-means clustering algorithm.

23. The method of claim 12, wherein the spatial data comprises x, y and z coordinates of each voxel and the degree data comprises a number of voxels to which each voxel is connected.

24. An article of manufacture comprising non-transitory computer readable media encoded with computer-executable instructions, which when executed by a computer, performs method steps for processing image data, the method steps comprising:
    gathering four-dimensional image data from a subject;
    extracting time series data, and spatial and degree data of each voxel of the subject;
    deriving at least one feature from the time series data;
    deriving at least one feature from the spatial and degree data;
    combining the at least one feature from the time series data, and the at least one feature from the spatial and degree data to generate combined data; and
    inputting the combined data to a classifier, wherein the classifier outputs a classification based on the combined data.

25. An apparatus for processing image data, comprising:
    a memory; and
    a processor coupled to the memory and configured to execute code stored in the memory for:
        gathering four-dimensional image data from a subject;
        extracting time series data, and spatial and degree data of each voxel of the subject;
        deriving at least one feature from the time series data;
        deriving at least one feature from the spatial and degree data;
        combining the at least one feature from the time series data, and the at least one feature from the spatial and degree data to generate combined data; and
        inputting the combined data to a classifier, wherein the classifier outputs a classification based on the combined data.

* * * * *